United States Patent [19]

Harris et al.

[11] Patent Number: 4,629,787

[45] Date of Patent: Dec. 16, 1986

[54] SUBSTITUTED CAPROLACTAM DERIVATIVES AS ANTIHYPERTENSIVES

[75] Inventors: Elbert E. Harris; Arthur A. Patchett, both of Westfield; Eugene D. Thorsett, Fanwood, all of N.J.

[73] Assignee: Merck & Co., Inc., Rahway, N.J.

[21] Appl. No.: 394,749

[22] Filed: Jul. 2, 1982

Related U.S. Application Data

[63] Continuation-in-part of Ser. No. 282,580, Jul. 13, 1981, abandoned, which is a continuation-in-part of Ser. No. 179,305, Aug. 18, 1980, abandoned.

[51] Int. Cl.[4] .................... C07D 223/10; A61K 31/55
[52] U.S. Cl. .................................. 540/528; 540/527; 540/524
[58] Field of Search ................. 260/239.3 R; 424/244, 424/273 R, 274

[56] References Cited

U.S. PATENT DOCUMENTS 4,052,511 10/1977 Cushman et al. .................. 546/208
4,129,371 12/1978 Ondetti et al. ...................... 546/208
4,154,960 5/1979 Ondetti et al. ...................... 546/208

OTHER PUBLICATIONS

Medicinal Chemistry, edited by Alfred Burger, Second Edition, Interscience Publishers, Inc., New York, 1960, pp. 566, 568, 580, 600, 601.

Primary Examiner—Robert T. Bond
Attorney, Agent, or Firm—Salvatore C. Mitri; Michael C. Sudol

[57] ABSTRACT

The invention in its broad aspects relates to caprolactam derivatives which are useful as angiotensin converting enxyme inhibitors and as antihypertensives.

3 Claims, No Drawings

SUBSTITUTED CAPROLACTAM DERIVATIVES AS ANTIHYPERTENSIVES

This is a continuation-in-part application of application Ser. No. 282,580 filed July 13, 1981, now abandoned, which, in turn, is a continuation-in-part of application Ser. No. 179,305 filed Aug. 18, 1980, now abandoned.

BACKGROUND OF THE INVENTION

The invention in its broad aspects relates to caprolactam derivatives which are useful as angiotensin converting enzyme inhibitors and as antihypertensives. The compounds of this invention can be shown by the following formula:

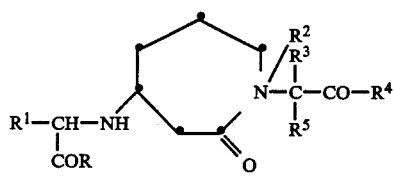

wherein

R and $R^4$ are the same or different and are hydroxy,
  lower alkoxy,
  lower alkenoxy,
  aryloxy (such as phenoxy),
  dilower alkylamino lower alkoxy (e.g., dimethylaminoethoxy),
  acylamino lower alkoxy (e.g., acetylaminoethoxy, nicotinoylaminoethoxy, succinimidoethoxy),
  acyloxy lower alkoxy (e.g., pivaloyloxyethoxy),
  arloweralkoxy (such as benzyloxy, p-methyoxybenzyloxy),
  hydroxy or dihydroxyloweralkoxy (such as glyceryloxy),
  amino,
  hydroxyamino;

$R^1$ is hydrogen,
  alkyl of from 1 to 12 carbon atoms which include straight and branched alkyl groups;
  alkenyl of from 2-12 carbon atoms which include straight and branched alkenyl groups;
  alkynyl of from 2-12 carbon atoms which include straight and branched alkynyl groups;
  cycloalkyl of from 3 to 10 carbon atoms;
  substituted loweralkyl wherein the substituent(s) can be halo, lower alkoxy, aryloxy (such as phenoxy), amino, lower alkylamino, aminoloweralkylthio, hydroxy, aminoloweralkoxy, diloweralkylamino, acylamino, (such as acetamido and benzamido), arylamino, (such as phenylamino), guanidino, phthalimido, mercapto, loweralkylthio, arylthio (such as phenylthio), carboxy, carboxamido or carboloweralkoxy,
  arloweralkyl, arloweralkenyl, heteroarlower alkyl or heteroarlower alkenyl (such as benzyl, styryl, indolylethyl, imidazolylmethyl, naphthylethyl),
  substituted arloweralkyl, or substituted heteroarlower alkyl wherein the aryl or heteroaryl substituent(s) is halo, dihalo, lower alkyl, hydroxy, lower alkoxy, amino, aminomethyl, phenyloxy, acylamino, diloweralkylamino, loweralkylamino, carboxyl, haloloweralkyl, acyl or aroyl; and the alkyl portion may be substituted by amino, hydroxyl or acylamino;

$R^2$ is hydrogen, lower alkyl, cyclic lower alkyl, amino lower alkyl, alkylaminoloweralkyl, hydroxyalkyl, acylaminoloweralkyl, dialkylamino lower alkyl including cyclic polyethyleneamino lower alkyl, arlower alkyl, aryl, substituted aryl wherein the substituent is halo, alkyl, aminoalkyl, or alkoxy, heteroaryl heteroarlower alkyl;

$R^3$ is hydrogen, lower alkyl, phenyl, phenyl lower alkyl, hydroxyphenyl lower alkyl, hydroxy lower alkyl, amino lower alkyl, acylamino lower alkyl, guanidino lower alkyl, imidazolyl lower alkyl, indolyl lower alkyl, mercapto lower alkyl or lower alkyl thio lower alkyl;

$R^5$ is hydrogen or lower alkyl;

and, the pharmaceutically acceptable salts thereof.

As used throughout this application, including the claims, and unless specified otherwise:

alkyl denotes straight and branched hydrocarbons of $C_1$-$C_{12}$ and loweralkyl denotes straight and branched hydrocarbons of $C_1$-$C_8$; alkenyl denotes straight and branched hydrocarbons of $C_2$-$C_{12}$ and loweralkenyl denotes straight and branched hydrocarbons of $C_2$-$C_8$, each of which contains a double bond; alkynyl denotes straight and branched hydrocarbons of $C_2$-$C_{12}$ and loweralkenyl denotes straight and branched hydrocarbons of $C_2$-$C_8$, each of which contains a triple bond; aryl and the prefix "ar" denote unsubstituted aromatic ring or rings of $C_6$-$C_{12}$ such as, for example, phenyl, naphthyl, biphenyl; acyl denotes a carboxylic acid derivative represented by the formula

wherein R is alkane, aralkane, arene, heteroarene, heteroaralkene, and substituted derivatives thereof so that aryl denotes, for example, alkanoyl, aroyl, aralkanoyl, heteroaryl, heteroaralkanoyl, and the like; cycloalkyl denotes an unsubstituted alkyl ring of $C_3$-$C_{10}$; hetero denotes the heteroatoms N, O or S; heteroaryl denotes an aryl group containing a heteroatom; heteroacycle denotes a saturated or unsaturated aromatic or non-aromatic cyclic compound containing a heteroatom; halogen or halo denote F, Br, Cl or I atoms; loweralkoxy denotes an alkyl group with O;

Exemplary loweralkyl or lower alkenyl groups include, for example, methyl, ethyl, propyl, isopropyl, butyl, isobutyl, t-butyl, pentyl, isopentyl, hexyl or vinyl, allyl, butenyl and the like, and exemplary heteroaryl groups include, for example, pyridyl, thienyl, furyl, indolyl, benzthienyl, imidazoyl, thiazolyl and quinolinyl.

Preferred are those compounds of Formula I wherein:

R and $R^4$ are the same or different and are hydroxy, lower alkoxy, and arloweralkoxy;

$R^2$ is hydrogen, loweralkyl, aminoloweralkyl, aralkyl, aryl, heteroaryl, or heteroaralkyl;

$R^5$ is hydrogen;

$R^1$ is alkyl having from 1 to 8 carbon atoms, substituted lower alkyl wherein the alkyl group has 1-5 carbon atoms and the substituent is amino, acylamino, hydroxy, aminoloweralkylthio, aminoloweralkoxy, arylthio, aryloxy or arylamino, aralkyl or heteroaralkyl wherein the alkyl portion has 1 to 3 carbon atoms (such as phenethyl or indolylethyl) or substituted arloweralkyl (phenyl lower alkyl or naphthyl lower alkyl) and substituted heteroarloweralkyl wherein the alkyl groups have 1-3 carbons optionally substituted with amino, hydroxy or acylamino and wherein the substituent(s) on the aryl or heteroaryl groups is halo, dihalo, amino, aminoalkyl, hydroxy, lower alkoxy, lower alkyl, phenoxy or benzoyl;

$R^3$ is hydrogen, lower alkyl, phenyl lower alkyl, hydroxy phenyl lower alkyl, amino lower alkyl, imidazolyl lower alkyl, indolyl lower alkyl, lower alkyl thio loweralkyl.

More preferred are compounds of Formula I wherein
$R^3$ is hydrogen, lower alkyl, amino lower alkyl, indolyl lower alkyl, phenyl lower alkyl;
$R^1$ is alkyl from 1 to 8 carbon atoms; substituted lower alkyl wherein the alkyl group has 1-5 carbon atoms and the substituent is amino, acylamino, hydroxy, aminoloweralkylthio, arylthio, aryloxy; aralkyl or heteroaralkyl wherein the alkyl portion has 1-3 carbon atoms (such as phenethyl or indolylethyl) or substituted arloweralkyl and substituted heteroarloweralkyl wherein the alkyl groups have 1-3 carbons optionally substituted with amino, acylamino or hydroxy and wherein the substituent(s) on the aryl and the heteroaryl groups is halo, ammino, aminoalkylhydroxy, or lower alkoxy;
$R^5$ is hydrogen;
$R^2$ is hydrogen, lower alkyl, aminoloweralkyl, aryl, or aralkyl;
R and $R^4$ are independently hydroxy, lower alkoxy, or arloweralkoxy.

Most preferred are compounds of Formula I wherein
$R^3$ is hydrogen or lower alkyl;
$R^1$ is alkyl of 1-8 carbons; substituted lower alkyl wherein the alkyl group has 1-5 carbon atoms and the substituent is amino, acylamino, arylthio, aryloxy; aralkyl or heteroaralkyl wherein the alkyl portion has 1-3 carbon atoms (such as phenethyl or indolylethyl); or substituted aralkyl or substituted heteroarloweralkyl wherein the alkyl groups have 1-3 carbons and the substituents on the aryl or heteroaryl groups are halo, amino, aminoalkyl, hydroxy, or loweralkoxy;
$R^5$ is hydrogen;
$R^2$ is hydrogen, lower alkyl, aminoloweralkyl or aryl;
R and $R^4$ are independently hydroxy, lower alkoxy or benzyloxy.

The preferred, more preferred and most preferred compounds also include the pharmaceutically acceptable salts thereof.

The products of Formula (I) and the preferred subgroups can be produced by one or more of the methods and subroutes depicted in the following equations. The definitions of R, $R^1$, $R^2$, $R^3$, $R^4$, and $R^5$ are the same as in Formula (I) except where noted.

METHOD I

A.

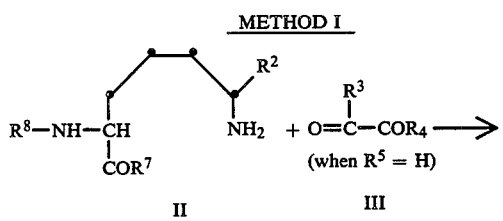

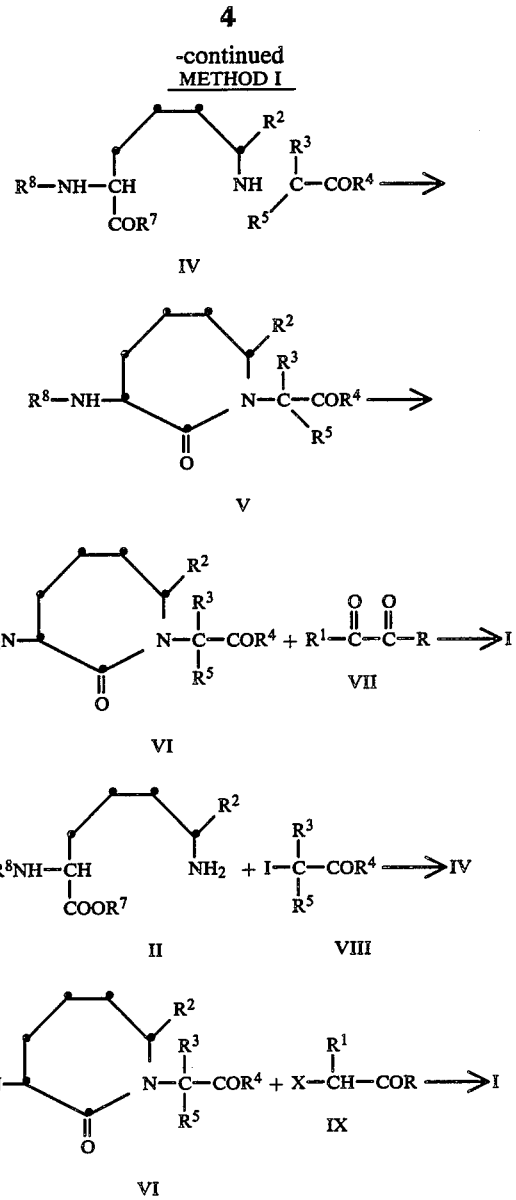

$R^7$=OH, $OR^9$
$R^9$=lower alkyl, aryl or aralkyl
$R^8$=benzyloxycarbonyl, t-butoxycarbonyl, other appropriate blocking groups known in peptide chemistry.
X=iodo or bromo Lysine [or an (ε-substituted lysine ($R^2 \neq H$) which can be prepared by the procedure of Blicke et al., J. Am. Chem. Soc, 76, 2317 (1954) followed by that of Tull et al., J. Org. Chem. 29, 2425 (1964)] is converted to the $N^\alpha$-protected derivative II by methods known in the art. Suitable protecting groups $R^8$ include the phthalimido, t-butoxycarbonyl, and benzyloxycarbonyl groups. $R^7$ may be OH or alkoxy as the methods below require and $R^4$ is as defined. Intermediate II is reductively coupled with the keto acid or ester III in aqueous solution, preferably near neutrality or in a suitable organic solvent, such as methanol or acetonitrile, in the presence of sodium cyanoborohydride or if protecting groups do not interefere with hydrogen and a suitable catalyst to yield IV. This intermediate, with $R^4$=OH and $R^7$=$OR^9$, is warmed in an organic solvent, such as acetonitrile, with a base such as triethylamine to obtain the perhydroazepinone V. The blocking group $R^8$ is removed by appropriate known methods, and the resulting compound VI is reductively coupled with keto acid, ester, etc. VII to obtain I. Substituents at R and $R^4$ may be altered by standard methods if desired.

Intermediate II may also be alkylated with a haloester such as VIII.

Furthermore, intermediate IV with $R^4$ not OH and $R^7$=OH may be cyclized to V by the use of dicyclohexylcarbodiimide and N-hydroxysuccinimide in a suitable solvent such as DMF or methylene chloride. Other known peptide coupling methods may also be used if desired.

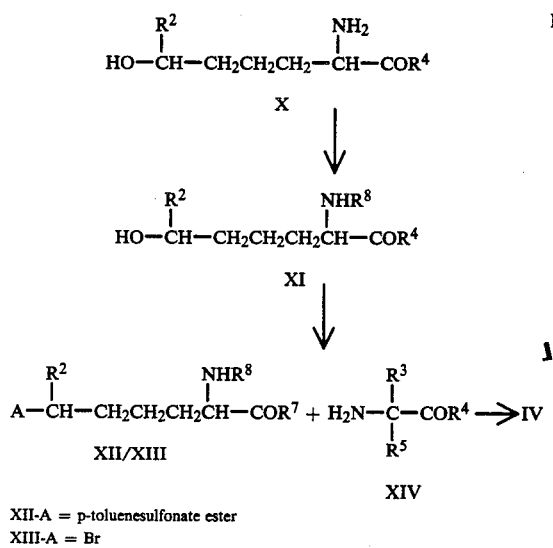

XII-A = p-toluenesulfonate ester
XIII-A = Br

Alternatively a hydroxyaminoacid X [Gandry, Can. J. Res., 26B, 387 (1948)] is converted to the N-protect hydroxy acid XI by established techniques, then the terminal hydroxyl is activated by known methods such as conversion to the tosyl ester XII or to the bromide XIII. Reaction with amino acid XIV affords the intermediate IV, which may be converted to I as described above.

METHOD II

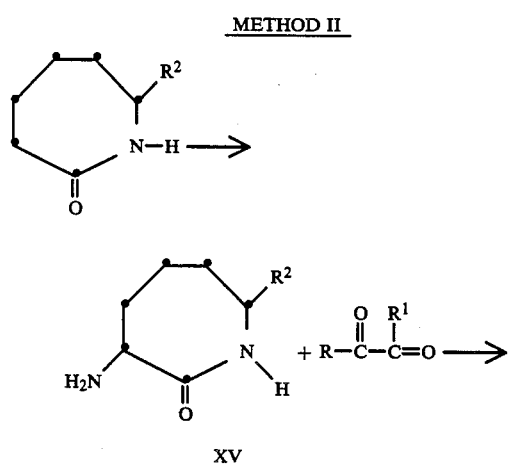

-continued
METHOD II

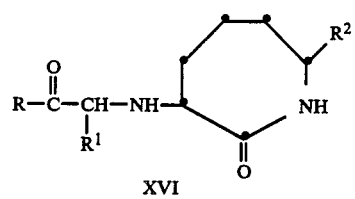

XVI

XVI + VIII ⟶ I

Substituted caprolactams ($R^2 \neq H$), are conveniently prepared via Beckman ring expansion of the corresponding 2-substituted cyclohexanone oximes using standard reaction conditions. These caprolactams can then be halogenated and converted to 3-amino derivatives via displacement reactions described, for example, by Blacket, et al. and Tull, et al. above; Wineman, et al., J. Am. Chem. Soc. 80, 6233 (1958) and Francis et al., J. Am. Chem. Soc. 80, 6238 (1958). Aminolactams XV are then alkylated on the exocyclic nitrogen using reagents VII or IX by the methods described above to obtain XVI. Alkylation of XVI with VIII in the presence of a strong base such as sodium hydride in a solvent such as DMF or THF affords I.

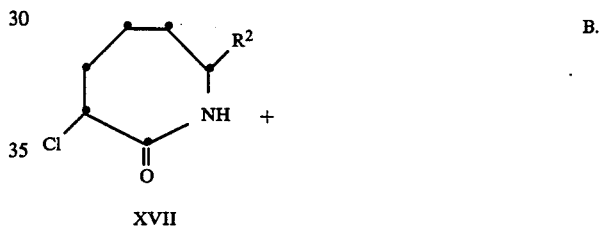

XVII

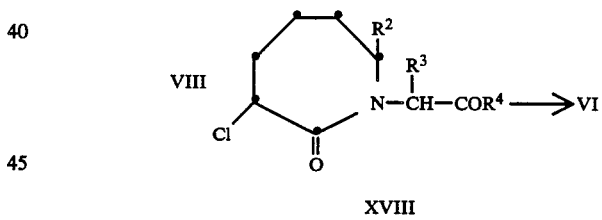

XVIII

The halocaprolactam XVII (Blicke and Tull cited above) can also be alkylated with reagent VIII in the presence of a strong base such as sodium hydride in a suitable solvent such as DMF or THF to obtain the alkylated halolactam XVIII. Treatment with azide ion followed by catalytic hydrogenation affords the intermediate VI described above.

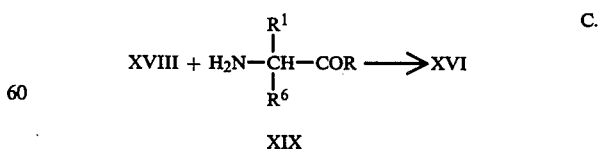

XIX

The halocaprolactam XVII is reacted with the amino acid derivative XIX to obtain the intermediate XVI for conversion to I as described above.

The starting materials which are required for the above processes herein described are known in the literature or can be made by known methods from known starting materials.

In products of general Formula (I), the carbon atoms to which, $R^1$, $R^2$ and $R^3$ are attached and the ring carbon atom to which the fragment

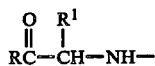

is attached may be asymmetric. The compounds accordingly exist in diastereoisomeric forms or as enantiomers or mixtures thereof. The above described syntheses can utilize racemates, enantiomers or diastereomers as starting materials and intermediates. When diastereomeric products result from the synthetic procedures, the diastereomeric products can be separated by chromatographic or fractional crystallization methods. When racemic products result, they may be resolved by crystallization of salts of optically active acids or bases or by other methods known in the art. The asymmetric carbon atoms specified above may be in two configurations (S or R) and both are within the scope of this invention, although S is generally preferred except for the configurations at the carbon to which $R^2$ is attached as exemplified in specific compounds of this invention.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases, e.g., dicyclohexylamine, N-methyl-D-glucamine, salts with amino acids like arginine, lysine and the like. Also salts with organic and inorganic acids may be prepared; e.g., HCl, HBr, $H_2SO_4$, $H_3PO_4$, methanesulfonic, toluenesulfonic, maleic, fumaric, camphorsulfonic acids. The nontoxic physiologically aceptable salts are particularly valuable, although other salts are also useful, e.g., in isolating or purifying products.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus blood-pressure lowering results from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension., See, for example. D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136, (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.*, 125, 96 (1967).

Thus, the compounds of the invention are useful in treating hypertension. They are also of value in the management of adute and chronic congestive heart failure, in the treatment of secondary hyperaldosteronism, scleroderma, primary and secondary pulmonary hyertension, renal failure and renal vascular hypertension, and in the management of vascular disorders such as migraine. The application of the compounds of this invention for these and similar disorders will-be apparent to those skilled in the art.

In the management of hypertension and those clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention cah be administered to patients in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 200 mg per patient per day which can be administered in single or multiple doses. Preferably, the dosage range will be about 2.5 to 100 mg per patient per day.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, hydroflumethiazide, metolazone, metoprololtartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, rifedipine, verapamil, diltiazam, flumethiazide, bendroflumethiazide, atenolol, (+)-4-[3-{[2-(1-hydroxycyclohexyl)ethyl]-4-oxo-2-thiazolidinyl}propyl}benzoic acid, bumetanide, prazosin, propranolol, *Rauwolfia serpentina*, rescinnamine, reserpine, spironolactone, timolol, trichlormethiazide, benzthiazide, quinethazone, triamterene, acetazolamide, aminophylline, cyclothiazide, merethoxylline procaine, and the like, as well as admixtures and combinations thereof.

Typically, the individual daily dosages for these combinations can range from about one-fifth of the maximum recomended levels for the entities when they are given singly.

To illustrate these combinations, one of the antihypertensives of this invention effective clinically in the 2.5–100 milligrams per day range can be effectively combined at levels at the 0.5–100 milligrams per day range with the following compounds at the indicated per day dose range: hydrochlorothiazide (10–100 mg), timolol (5–60 mg), methyl dopa (65–2000 mg), the pivaloyloxyethyl ester of methyl dopa (30–1000 mg), indacrinone and variable ratios of its enantiomers (25–150 mg) and (+)-4-{3-{-[2-(1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus timolol (5–60 mg) plus converting enzyme inhibitor of this invention (0.5–100 mg) or hydrochlorothiazide (10–100 mg) plus amiloride (5–20 mg) plus converting enzyme inhibitor of this invention (0.5–100 mg) are effective combinations to control blood pressure in hypertensive patients.

Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 0.5 to 100 mg. of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practive. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instace, tablets may be coated with shellac, sugar or both. A syrup or elixir may contain the active compund, sucrose as a sweetening agent, methyl and propyl parabens as preservarives, a dye and a flavoring such as cherry or orange flavor.

Sterile compositions for injection can be formulated according to conventional pharmaceutical practice by dissolving or suspending the active substance in a vehicle such a water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by column chromatography or fractional crystallization.

EXAMPLE 1

1-Carboxymethyl-3-(S)-[(1-carboxy-3-phenylpropyl)amino]perhydroazepin-2-one

Dissolve 10.45 g of $N^\alpha$-Boc-$N^\epsilon$-Cbz-L-lysine in 125 ml methanol and 17 ml water. Neutralize the solution with 27.5 ml of 0.5M cesium carbonate solution and concentrate the resulting solution to a syrup at aspirator pressure and 35° C. Dissolve the syrup in 100 ml. dimethylformamide and concentrate; repeat once more. Dissolve the residue in 75 ml. dimethylformamide and 2.7 ml. methyl iodide. Stir the reaction mixture overnight at room temperature then remove the dimethylformamide under vacuum (oil pump). Add 250 ml. water to the residue and extract into 150 ml. ethyl acetate. Wash the ethyl acetate extract twice with 100 ml. portions of water then dry the organic phase over MgSO$_4$. Filter and concentrate the dried solution in vacuo to obtain $N^\alpha$-Boc-$N^\epsilon$-Cbz-L-lysine methyl ester.

Prepare a solution of 11.5 g. $N^\alpha$-Boc-$N^\epsilon$-Cbz-L-lysine methyl ester and 3.3 g. glyoxylic acid hydrate in 80 ml. methanol. Add 2 g. 10% palladium on charcoal catalyst and hydrogenate for 3 hours at room temperature and an initial pressure of 40 psig. Filter the reaction mixture to remove catalyst and wash the catalyst with methanol. Concentrate the combined filtrate and washings in vacuo to $N^\alpha$-Boc-$N^\epsilon$-carboxymethyl-L-lysine methyl ester.

Add 8.0 g. $N^\alpha$-Boc-$N^\epsilon$-carboxymethyl-L-lysine methyl ester and 4.7 ml. triethylamine to 2.8 L of acetonitrile and reflux the mixture for 3 days. Cool the reaction and concentrate at aspirator pressure on the rotary evaporator to a yellow glass. Dissolve the glass in 175 ml. CH$_2$Cl$_2$ and wash three times with 55 ml. portions of 20% citric acid and then twice with 55 ml. portions of 1N NaHCO$_3$. Combine the NaHCO$_3$ washes and adjust to pH 3 with 40% citric acid solution. Extract the acidified solution with six 60 ml. portions of CH$_2$Cl$_2$. Dry the organic extract over MgSO$_4$, filter, then concentrate at aspirator pressure to 3-(S)-t-butoxycarbonylamino-1-carboxymethylperhydroazepin-2-one.

tlc (silica, 20 Ethyl acetate: 5 pyridine: 1 acetic acid: 1 water) Rf=0.8

Dissolve 2.1 g 3-(S)-t-butoxycarbonylamino-1-carboxymethylperhydroazepin-2-one in 70 ml ice cold 4N HCl in ethyl acetate and stir at 0° C. for 1 hour. Remove the cooling bath and bubble nitrogen through the mixture for 20 minutes. Filter the precipitate and wash with ether to obtain 3-(S)-amino-1-carboxymethylperhydroazepin-2-one hydrochloride as a white solid. Filter the combined filtrate and washings to obtain additional product.

Suspend 4.45 g 2-oxo-4-phenylbutyric acid in 25 ml water and adjust the pH to 7 with 50% NaOH. Add 1.14 g 3-(S)-amino-1-carboxymethylperhydroazepin-2-one hydrochloride and again adjust the pH to 7 with 50% NaOH. Dilute the resulting solution with water to a total volume of 60 ml then add 0.943 g sodium cyanoborohydride. After 2 days at room temperature, add 50 ml Dowex 50 (H+) and stir the mixture for 1 hour. Extract the mixture with ether and then add the Dowex 50 and aqueous portion to the top of a 100 ml. column of Dowex 50 (H+). Elute first with water until the eluate is neutral and then with 2% pyridine in water until no further product elutes (ninhydrin detection). Concentrate the product containing fractions at aspirator pressure, redissolve the residue in 50 ml water and freeze dry. Isolate the 1-carboxymethyl-3-(S)-[(1-carboxy-3-phenylpropyl)amino]perhydroazepin-2-one as a white hygroscopic solid.

Mass spec.: M+348; 330 (M—$H_2O$); 303 (M—$CO_2H$).

NMR: ($D_2O$, TSS). δ1.4–2.5 (m, 8H); δ2.6–3.1 (m, 2H); δ3.3–4.0 (m, 3H); δ4.1–4.3 (m, 3H); δ7.4 (S, 5H).

EXAMPLE 2

1-Carboxymethyl-3-(S)-[(1-ethoxycarbonyl-3-phenylpropyl)amino]perhydroazepin-2-one Dissolve 280 mg. 1-carboxymethyl-3-(S)-aminoperhydro-2-azepinone hydrochloride in 50 ml water and adjust the pH to 6.8 with benzyltrimethylammonium hydroxide solution. Freeze dry the reaction mixture and dissolve the residue in 10 ml absolute ethanol. Add 1.3 g ethyl 2-oxo-4-phenylbutyrate and 7.5 g powdered 4A molecular sieves. To this stirred mixture, add over a period of four hours 357 mg sodium cyanoborohydride in four equal portions then stir the reaction at room temperature overnight. Filter the reaction and wash the filter cake with ethanol. Concentrate the combined filtrate and washings in vacuo then dissolve the residue in 40 ml. water. Add 10 ml Dowex 50 (H+) and 25 ml ether and stir the mixture for one hour. Remove the ether layer and extract the aqueous portion again with ether. Remove the ether and apply the aqueous slurry onto a column of 20 ml Dowex 50 (H+). Elute first with water until the eluate is neutral and then with 2% pyridine in water until no further product elutes. Concentrate the product containing fractions in vacuo, dissolve the residue in water and lyophilize. Isolate 396 mg. of 1-carboxymethyl-3-(S)-[(1-ethoxycarbonyl-3-phenylpropyl)amino]perhydroazepin-2-one as a white powder.

NMR. ($D_2O$, TSS) δ1.2–1.5 (t, 3H); δ1.5–2.6 (m, 7H); δ2.5–3.2 (m, 2H); δ3.3–3.7 (m, 3H); δ3.8–4.6 (m, 6H); δ7.4 (S, 5H),

Mass spectrum: M+ 376; 331 (M—$C_2H_5O$); 317 (M—$CH_2CO_2H$); 303 (M—$CO_2C_2H_5$).

In the same manner react the 3-(S)-amino-1-carboxymethylperhydroazepin-2-one with ethyl 4-(3-indolyl)-2-oxobutyrate to obtain 1-carboxymethyl-3-(S)-[(1-ethoxycarbonyl-3-(3-indolyl)propyl)amino]perhydroazepin-2-one. Standard alkaline hydrolysis (as in Example 3) of this material yields 1-carboxymethyl-3-(s)-[(1-carboxy-3-(3-indolyl)propyl)amino]perhydroazepin-2-one. Alternatively, esterification in HCl-ethanol affords 1-ethoxycarbonylmethyl-3-(S)-1-(1-ethoxycarbonyl-3-(3-indolyl)lpropyl)amino]perhydroazepin-2-one.

EXAMPLE 3

1-(1-Carboxyethyl)-3-(S)-[(1-carboxy-3-phenylpropyl)amino]-perhydroazepin-2-one

Dissolve 7.6 g $N^\alpha$-Boc-$N^\epsilon$-Cbz-L-lysine and 2.04 g methyl pyruvate in 75 ml methanol. Add 2 g 10% palladium on charcoal and hydrogenate at an initial pressure of 40 psig for 3 hours at room temperature. Filter the solution and concentrate the filtrate at aspirator pressure to obtain $N^\alpha$-Boc-$N^\epsilon$-(1-methoxycarbonylethyl)-L-lysine.

Dissolve 4.76 g. of this ester and 1.64 g N-hydroxysuccinimide in 250 ml dimethylformamide, cool the solution to 0° and then add a solution of 3.24 g dicyclohexylcarbodiimide in 10 ml. dimethylformamide. Store the reaction mixture at 4° C. for 2 days. Remove the solvent in vacuo (oil pump) and take up the residue in chloroform. Filter the mixture and then concentrate the filtrate. Dissolve the residue in 1:1 ethyl acetate-hexane, filter and chromatograph on silica gel using 7:3 hexane: ethyl acetate as eluent. Combine those fractions containing the desired product and concentrate at aspirator pressure to afford 1.75 g. 3-(S)-t-butoxycarbonyl-amino-1-(1-methoxycarbonylethyl)perhydroazepin-2-one. tlc (silica, 7:3 Hexane: Ethyl acetate) Rf 0.5 NMR ($CDCl_3$, TMS) δ1.2–2.4 (m, 18H); δ3.2–3.6 (broad 2H); δ3.7 (S, 3H); δ4.1–4.6 (broad, 1H); δ4.5–5.4 (2q, 1H); δ5.8–6.1 (broad, 1H). Mass spectrum: M+314 (weak); 258 (M—$C_4H_8$); 241 (M—$C_4H_9O$).

Dissolve 2.59 g 3-(S)-t-butoxycarbonylamino-1-(1-methylcarbonylethyl)perhydroazepin-2-one in 10 ml. methanol and 10 ml water and add 0.5 ml 50% NaOH solution. Store the mixture at room temperature for 2 hours and then concentrate at aspirator pressure to a syrup. Dissolve the syrup in water and chill the solution in an ice bath. Add 6N hydrochloric acid to pH 2 then extract the solution several times with ethyl acetate. Dry the combined extracts over $MgSO_4$, filter and concentrate the filtrate at aspirator pressure and isolate 3-(S)-t-butoxycarbonylamino-1-(1-carboxyethyl)perhydroazepin-2-one as an oil (2.04 g) which is a mixture of diastereomers. Separate the isomers on a column of XAD2 resin at 50° C. using 0.1N $NH_4OH$ containing 6% acetonitrile as eluent. Isolate the ammonium salt of the desired isomer as the one which elutes first (u.v. and refractive index detection).

Treat 610 mg of the desired isomer with 20 ml 4N hydrogen chloride in ethyl acetate at 0° for 1 hours. Warm the mixture to room temperature and purge with nitrogen for 20 minutes then concentrate the solution to dryness. Dissolve the residue in water and reconcentrate to obtain 3-(S)-amino-1-(1-carboxyethyl)perhydroazepin-2-one hydrochloride.

Dissolve 422 mg of 3-(S)-amino-1-(1-carboxyethyl)-perhydroazepin-2-one hydrochloride in water and adjust the pH to 6.8 with 2M tetrabutylammonium hydroxide. Lyophilize the solution and dissolve the residue in 10 ml absolute ethanol. Add 1.98 g ethyl 2-oxo-4-phenylbutyrate and 7 g. powdered 4A molecular sieves. Add a solution of 357 mg. sodium cyanoborohydride in 3 ml absolute ethanol at a rate of 0.5 ml/hour. After the addition is complete, stir the reaction mixture overnight at room temperature. Filter the reaction mixture, wash the filter cake with ethanol and concentrate the combined filtrate and washings at aspirator pressure. Dissolve the residue in water and add 20 ml ether and 20 ml Dowex 50 (H+). Stir the mixture for 1 hour then draw off the ether layer.

Extract the aqueous suspension twice more with ether then add the aqueous portion to a column of 100 ml of Dowex 50 (H+). Elute with water until the eluate is neutral then elute with 2% pyridine in water and collect 600 ml of eluent. Concentrate the eluent in vacuo, dissolve the residue in water and lyophilize. Isolate 1-(1-carboxyethyl)-3-(S)-[(1-ethoxycarbonyl-3-phenylpropyl)amino]perhydroazepin-2-one as a powder (652 mg.).

NMR: ($D_2O$, TSS) δ1 2–1.5 (t+d, 6H); δ1.5–2.6 (m, 8H); δ2.6–3.1 (m, 3H); δ3.2–3.6 (broad, 2H); δ3.9–4.5 (q+m, 4H); δ7.3 (S, 5H).

Mass spectrum: (as monotrimethylsilyl derivative) M+=462; 447 (M—$CH_3$); 389, 373.

Dissolve 110 mg of the ethyl ester in 1 ml 1N sodium hydroxide and heat the solution at 45° overnight. Chromatograph the reaction mixture on a Dowex 50 (H+) column, eluting first with water then with 2% pyridine in water. Concentrate in vacuo those fractions containing 1-(1-carboxyethyl)-3-(S)-[(1-carboxy-3-phenylpropyl)amino]perhydroazepin-2-one and lyophilize.

Mass Spectrum (as bistrimethylsilyl derivative): M+, 506; 491 (M+—CH₃); 391 (M+—CO₂TMS).

EXAMPLE 4

1-Carboxymethyl-3-(S)-[(1-carboxyethyl)amino]perhydroazepin-2-one

Dissolve 196 mg benzyl pyruvate and 128 mg 3-(S)-aminoperhydroazepin-2-one (Adamson, *J. Chem. Soc.*, 1943, 39) in 5 ml tetrahydrofuran. Add 0.5 q anhydrous magnesium sulfate then add dropwise over 25 min. a solution of 63 mg sodium cyanoborohydride in 5 ml tetrahydrofuran. After completion of the addition, stir the reaction an additional one hour. Filter the reaction and concentrate the filtrate in vacuo. Dissolve the residue in ethyl acetate, wash with water and brine, dry over magnesium sulfate, filter and concentrate the filtrate in vacuo to 237 mg of a clear oil. Chromatograph the crude product on silica gel eluting with ethyl acetate: acetonitrile (95:5). Concentrate those fractions containing 3-(S)-[(1-benzyloxycarbonylethyl)amino]perhydroazepin-2-one.

tlc: (silica, ethyl acetate:acetonitrile, 95:5) Rf=0.23.

NMR (CDCl₃, TMS): 1.2–2.3 (m, 10H); δ2.8–3.7 (q+m, 5H); δ5.2 (S, 2H); δ6.8 (broad, 1H); δ7.3 (S, 5H).

Dissolve 320 mg of 3-(S)-[(1-benzyloxycarbonylethyl)amino]perhydro-2-azepinone in 10 ml tetrahydrofuran and add 0.80 ml of 1.37 M potassium t-amyloxide in t-amyl alcohol. After 1–2 min., add a solution of 310 mg benzyl iodoacetate in 2 ml tetrahydrofuran in one portion. After 65 hours at room temperature, pour the reaction into water. Extract with ether, wash the organic phase with water then with brine. Concentrate the ether solution in vacuo to 440 mg of crude product. Chromatograph the crude product on silica gel eluting with ethylacetate: acetonitrile (95:5). Combine the fractions containing 1-benzyloxycarbonylmethyl-3-(S)-[(1-benzyloxycarbonylethyl)amino]perhydroazepin-2-one and concentrate to a colorless oil.

NMR: (CDCl₃, TMS) δ1.2–2.2 (m+d, 9H); δ3.2 (broad, 2H); δ3.5–4.0 (m, 2H); δ4.1–5.0 (m, 2H); δ5.1–5.2 (2S, 4H); δ6.2 (broad, 1H); δ7.3 (S, 10H).

Dissolve the diester in aqueous ethanol, and hydrogenate over 10% palladium on charcoal at an initial pressure of 40 psig. Filter the reaction mixture and concentrate the filtrate in vacuo to obtain 1-carboxymethyl-3-(S)-[(1-carboxyethyl)amino]perhydroazepin-2-one.

EXAMPLE 5

1-(1-Carboxyethyl)-3-[(1-carboxy-3-phenylpropyl)amino]perhydroazepin-2-one

Dissolve 1.5 g 3,3-dichloroperhydroazepin-2-one [W.C. Francis et al., *J. Am. Chem. Soc.*, 80, 6238 (1958)] in 5 ml dimethylformamide and purge the solution with nitrogen. Add 6.05 ml of 1.37M potassium t-amyloxide in t-amyl alcohol and stir for 5 minutes. Add 2.25 g ethyl 2-iodopropionate then stir the mixture for 4 days at room temperature. Concentrate the reaction in vacuo, add toluene and concentrate again. Add a second portion of toluene, filter and concentrate the filtrate in vacuo. Chromatograph the residue on silica gel with hexane:ethyl acetate (7:3). Collect those fractions containing product and isolate 786 mg of 3,3-dichloro-1-(1-ethoxycarbonylethyl)perhydroazepin-2-one.

tlc: silica, hexane:ethyl acetate (7:3) Rf=0.5

NMR (CDCl₃, TMS) δ1.1–2.3 (m+t+d, 10H); δ2.5–2.8 (m, 2H); δ3.4–3.7 (m, 2H); δ4.2 (q, 2H): δ5.05 (q, 1H).

Saturate 20 ml. methanol with ammonia and add 781 mg of the dichloro compound and 1 ml water. Hydrogenate the solution over 50 mg 10% palladium on charcoal at an initial pressure of 40 psig. Filter the mixture and concentrate the filtrate in vacuo. Triturate the residue with 50 ml of chloroform, filter and concentrate the filtrate. Chromatograph the residue on silica gel eluting with hexane:ethyl acetate (7:3). Collect and concentrate those fractions containing 3-chloro-1-(1-ethoxycarbonylethyl)perhydroazepin-2-one as a mixture of diastereomers.

Mass spectrum: M+247; 212 (M+—Cl); 202 (M+—C₂H₅O).

Dissolve 5.4 g of this monochloro ester and 1.63 g sodium azide in a mixture of 5 ml ethanol and 9 ml water. Reflux the mixture overnight, cool, and concentrate in vacuo. Extract the residue into chloroform, filter, dry the filtrate over magnesium sulfate, filter and concentrate the filtrate. Chromatograph the residue on silica gel eluting with hexane:ethyl acetate (9:1). Combine and concentrate those fractions containing 3-azido-1-(1-ethoxycarbonylethyl)perhydroazepin-2-one.

Infra red spectrum: γN=N=N, 2100 cm⁻¹; γC=O, ester, 1740 cm⁻¹; γC=O, amide, 1650 cm⁻¹.

Hydrogenate this azide in aqueous ethanol over 10% palladium on charcoal. Isolate the 3-amino-1-(1-ethoxycarbonylethyl)perhydroazepin-2-one after filtration and concentration of the filtrate in vacuo.

Hydrolyze this amino ester with 1N sodium hydroxide and isolate 3-amino-1-(1-carboxyethyl)perhydroazepin-2-one after chromatography on Dowex 50 (H+) using first water then 2% pyridine in water as eluent.

Convert this amino acid to 1-(1-carboxy-ethyl)-3-[(1-carboxy-3-phenylpropyl)amino]perhydroazepin-2-one as described in Example 3.

EXAMPLE 6

1-(1-Carboxyethyl)-3-[(1-carboxy-3-phenylpropyl)aminoperhydroazepin-2-one

Prepare a solution of chromous chloride in an oxygen-free system by adding a solution of 2.66 g chromium trichloride hexahydrate in 5 ml 5% hydrochloric acid to 654 mg zinc dust. After stirring for 1 hour remove excess zinc by filtration under nitrogen. Add a solution of 3,3-dichloro-1-(1-ethoxycarbonylethyl)perhydroazepin-2-one (prepared as described in Example 5) in 5 ml oxygen-free acetone to the above filtrate. After 30 minutes remove the acetone in vacuo, add 15 ml water and extract the aqueous mixture with three 20 ml portions of dichloromethane. Concentrate the organic extracts in vacuo and chromatograph the residue on silica gel eluting with hexane/ethyl acetate (7:3). Combine fractions containing 3-chloro-1-(1-ethoxycarbonylethyl)perhydroazepin-2-one.

tlc (silica, hexane:ethyl acetate, 7:3) Rf: 0.58

Convert this monochloro ester to 1-(1-carboxyethyl)-3-[(1-carboxy-3-phenylpropyl)amino]perhydroazein-2-one as described in Example 5.

EXAMPLE 7

1-Carboxymethyl-3-(S)-[(1-carboxy-2-phenylethyl)amino]perhydroazepin-2-one

Prepare an aqueous solution of 500 mg 3-(S)-amino-1-carboxymethylperhydroazepin-2-one in 5 ml water. Adjust the pH to 6 with 1N sodium hydroxide solution and add 15 ml water. React this amine with 2.24 g sodium phenylpyruvate monohydrate and 400 mg sodium cyanoborohydride as described in Example 1. Purify 370 mg of the crude product on an LH-20 column and isoalte 240 mg of 1-carboxymethyl-3-(S)-[(1-carboxy-2-phenylethyl)amino]perhydroazepin-2-one.

Mass spectrum (bistrimethylsilyl derivative): M+478; 463 (M+—CH$_3$); 361 [M+CO$_2$Si(CH$_3$)$_3$]

NMR (D$_2$O +NaOD): δ1.2–2.0 (m, 6H); δ2.7–3.0 (d, 2H); δ3.0–4.3 (m, 6H); δ7.2 (s, 5H).

EXAMPLE 8

1-Carboxymethyl-3-(S)-[(1-ethoxycarbonyl-4-phenylbutyl) amino]perhydroazepin-2-one React 1.08 g 3-(S)-amino-1-carboxymethylperhydroazepin-2-one hydrochloride, 5.3 g ethyl 2-oxo-5-phenylpentanoate, 0.49 g triethylamine and 630 mg sodium cyanoborohydride as described in Example 2. Purify the crude product by chromatography on LH 20 and isolate the desired ester.

NMR (CDCl$_3$+TMS): δ1.3 (t, 3H); δ1.4–2.4 (m, 10H); δ2.7 (broad t, 2H); δ2.9–3.9 (m, 5H); δ3.9–4.5 (m, 4H); δ7.3 (s, 5H).

Mass spectrum: M+390; 372 (M+—H$_2$O ); 361 (M+—C$_2$H$_5$); 345 (M+OC$_2$H$_5$).

EXAMPLE 9

1-Carboxymethyl-3-(S)-[(1-carboxy-4-phenylbutyl)amino]perhydroazepin-2-one

Hydrolyze 100 mg 1-carboxymethyl-3-(S)-[(1-ethoxycarbonyl-4-phenylbutyl)amino]perhydroazepin-2-one with sodium hydroxide as described in Example 3. Purify the reaction product on Dowex 50 and isolate the diacid.

NMR (D$_2$O) δ1.4–2.4 (m, 10H); δ2.8 (t, 2H); δ3.2–4.0 (m, 4H); δ4.0–4.8 (m, 3H); δ7.4 (s, 5H).

Mass spectrum: M+362; 344 (M+—H$_2$O); 317 (M+—CO$_2$H)

EXAMPLE 10

1-Carboxymethyl-3-(S)-[(1-ethoxycarbonyl-4-methylpentyl)amino]perhydroazepin-2-one Dissolve 815 mg 3-(S)-amino-1-carboxymethylperhydroazepin-2-one hydrochloride in 5 ml water, adjust the pH to 6 with 1N sodium hydroxide and lyophilize. React this salt with 3.0 g ethyl 2-oxo-5-methylhexanoate and 660 mg sodium cyanoborohydride as described in Example 2. Purify the crude product by chromatography on LH-20 and isolate 476 mg of pure 1-carboxymethyl-3-(S)-[(1-ethoxycarbonyl)-4-methylpentyl)amino]perhydroazepin-2-one.

NMR (D$_2$O, Dioxane at δ3.6 int. std.): δ0.7 (d, 6H); δ1.1 (t, 3H); δ1.3–2.2 (m, 11H); δ3.0–3.4 (broad, 2H); δ3.5–4.3 (m, 6H).

Mass spectrum: (monotrimethylsilyl derivative ) M+, 414; 399 (M+—CH$_3$); 341 (M+—CO$_2$C$_2$H$_5$)

EXAMPLE 11

1-Carboxymethyl-3-(S)-[(1-carboxy-4-methylpentyl)amino]perhydroazepin-2-one

Hydrolyze 210 mg of 1-carboxymethyl-3-(S)-[(1-ethoxycarbonyl-4-methylpenyl)amino]perhydroazepin-2-one with sodium hydroxide as described in Example 3. Purify the hydrolyzed ester on Dowex 50 (H+) and isolate the diacid.

NMR: (D2O, Dioxane at δ3.6): δ0.7 (d, 6H); δ0.9–2.3 (m, 11H); δ2.9–4.4 (m, 6H).

Mass spectrum: M+, 314; 296 (M+—H$_2$O); 269 (M+—CO$_2$H).

EXAMPLE 12

3-[t-Butoxycarbonylamino]-1-(1-carboxyethyl)perhydroazepin-2-one

Hydrogenate a solution of 7.6 g N$^\alpha$-t-butoxycarbonyl-N$^\epsilon$-benzyloxycarbonyl-L-lysine and 1.81 ml methylpyruvate in 75 ml methanol over 10% palladium on carbon in the standard fashion. After filtration and concentration isolate N$^\alpha$-t-butoxy-carbonyl-N$^\epsilon$-(1-methoxycarbonyl-1-ethyl)lysine.

Dissolve 4.76 g of the lysine derivative, 1.64 g. of N-hydroxysuccinimide and 3.24 g dicyclohexylcarbodiimide in 250 ml. of DMF. Store this reaction mixture at 0° C. for two days. Concentrate the reaction in vacuo and dissolve the residue in ethyl acetate. Filter and purify the product by silica gel chromatography. Isolate the purified 3-(S)-t-butoxycarbonylamino-1-(1-methoxycarbonylethyl)perhydroazepin-2-one.

Hydrolyze 2.59 g of this ester in 10 ml methanol and 10 ml H$_2$O containing 0.5 ml 50% NaOH. After two hours at room temperature, concentrate the reaction in vacuo, add water, chill to 0°, acidify to pH 2 and extract with ethyl acetate. Dry the extracts, filter and concentrate to obtain the acid.

Apply this acid to a column of milled XAD-2 resin maintained at 50° and elute with 6% CH$_3$CN:94% 0.1M NH$_4$OH to separate the diastereomers.

Isolate the diastereomer which elutes first from the column (Isomer A) as the ammonium salt. Convert this compound to 3-(S)-t-butoxycarbonylamino-1-(1-carboxyethyl)perhydroazepin-2-one by careful acidification of its aqueous solution. Recrystallize the acid from ether-petroleum ether. M.p. 125°–126°. [α]$_{Na}^{25°}$ = −33.6° (C=1.8, EtOH). Anal. (C$_{13}$H$_{24}$NO$_5$) Calc.: C, 55.98; H, 8.05; N, 9.32. Found: C, 55.87; H, 8.09; N, 9.37.

Isolate the diastereomer which elutes second (Isomer B), 1-(1-carboxy-1-ethyl)-3-(S)-t-butoxycarbonylaminoperhydroazepin-2-one. NMR (D$_2$O, TSS) δ1.3–1.5 (s+d, 12H); δ1.6–2.2 (m, 6H); δ3.3–3.7 (m, 2H); δ4.4 (m, 1H); δ4.9 (q, partially obscured by H$_2$O, 1H).

EXAMPLE 13

1-Ethoxycarbonylethyl-3-(S)-[(1-carboxy-3-phenylpropyl)-amino]perhydroazepin-2-one 3-(S)-t-Butoxycarbonylamino-1-(1-carboxyethyl) perhydroazepin-2-one (Isomer A) (2 g), prepared as in Example 12, was treated with thionyl chloride in absolute ethyl alcohol to provide 2.07 g of the 3-(S)-amino-1-(1-ethoxycarbonyl)perhydroazepin-2-one hydrochloride. This material, following careful neutralization with ethanolic sodium ethoxide, was condensed with benzyl 2-keto-4-phenylbutyrate in the same manner as Example 1, the keto ester having been prepared by thionyl chloride treatment of the ketoacid in benzyl alcohol and purified via the sodium bisulfite addition product. The diastereoisomeric mixture resulting from the reductive amination (10.6 g) was chromatographed over silica gel to yield the individual isomers:

Isomer A (first off the column) and isomer B (second off column). They were individually hydrogenated over 10% Pd/C in ethanol at atmospheric pressure to afford 299 mg of 1-ethoxycarbonylethyl-3-(S)-[(1-carboxy-3-phenyl-1-propyl)amino]perhydroazepin-2-one (Isomer A) and 762 mg of 1-ethoxycarbonylethyl-3-(S)-[(1-carboxy-3-phenyl-1-propyl)amino]perhydroazepin-2-one (Isomer B). The first isomer spontaneously changed from an oil to an amorphous solid (m.p. 104°–110° C.); nmr spectrum (CDCl$_3$) showed the aromatic proton singlet at 7.19 ppm, the ethyl quartet at 4.13 ppm, and the methyl doublet (1.27 ppm) superimposed on the ethyl triplet (1.21 ppm). The nmr spectrum (CDCl$_3$) of the second isomer showed the aromatic proton singlet at 7.26 ppm, the ethyl quartet at 4.19 ppm, the methyl doublet at 1.37 pm, and the ethyl triplet at 1.23 ppm.

EXAMPLE 14

1-Carboxymethyl-3-(S)-[(1-carboxy-5-phthalimidyl-1-pentyl)amino]perhydroazepin-2-one React 2.86 g 3-(S)-amino-1-benzyloxycarbonylmethylperhydroazepin-2-one hydrochloride, prepared from the acid (Example 1) by the method of S. Wang, *J. Org. Chem.*, 42, 1286 (1977), with 13.4 g benzyl 2-oxo-5-phthalimidylhexanoate and 1.73 g sodium cyanoborohydride as described in Example 39. Concentrate the reaction mixture in vacuo, dissolve the residue in H$_2$O and adjust to pH 1 with 6N HCl. After 5 min., adjust to pH 9.5 with 10% Na$_2$CO$_3$ and extract with ethyl acetate. Dry and concentrate the extract to obtain the crude diester. Chromatograph on silica gel using ethyl acetate-hexane (3:2) as eluent. Isolate the diastereomer which elutes second to obtain 2.27 g of diester.

Hydrogenate in the standard way 2.6 g of this diester dissolved in 15 ml dioxane, 5 ml H$_2$O and 0.1 ml. acetic acid using 10% palladium on charcoal as catalyst. Filter and concentrate the reaction mixture. Chromatograph the residue on LH-20 resin and isolate 1.35 g of the diacid.

tlc, silica gel, CHCl$_3$:CH$_3$OH—8.2 Rf=0.25.

Mass spectrum: M+ 445, m/e 400 (M+—CO$_2$H).

EXAMPLE 15

1-Carboxymethyl-3-(S)-[(5-amino-1-carboxy-1-pentyl)amino]perhydroazepin-2-one

Dissolve 550 mg of the first phthalimido diacid described in Example 14 in 5 ml CH$_3$OH containing 0.159 ml of N-methylhydrazine. Reflux the solution for 2 hours, then store at room temperature overnight. Filter, concentrate the filtrate in vacuo, then dissolve the residue in H$_2$O. Adjust the pH to 1 with HCl, heat on a water bath for 1 hour, then store the solution overnight at 4° C. Filter and concentrate the filtrate. Purify the crude product on LH 20 eluting with methanol.

Mass spectrum (tetra-trimethylsilyl deriv) M+ 603, m/e 588 (M+—2CH$_3$); 471 [M+—2CH$_3$—CO$_2$-Si(CH$_3$)$_3$].

In a similar manner, the second phthalimido diacid described in Exmple 14 may be converted to 1-carboxyethyl-3-(S)-[(5-amino-1-carboxy-1-pentyl)amino]perhydroazepin-2-one.

EXAMPLE 16

1-[(1-Benzyloxycarbonyl-5-phthalimidyl)pentyl]-3-[(1-carboxy-3-phenylpropyl)amino)]perhydroazepin-2-one Treat 302 mg of 1-[(1-benzyloxycarbonyl-5-phthalimidyl)pentyl]-3-(S)-(t-butyloxycarbonylamino)-perhydroazepin-2-one (prepared in Example 19) with 4M HCl in ethyl acetate, strip off the solvent in vacuo, take up in 20 ml of ethanol, add 471 mg of 2-keto-4-phenylbutyric acid, 112 mg of sodium methylate in 10 ml of ethanol, and 2 g of molecular sieves; stir for 1 hour. Then add over a 10-hour period a solution of 140 mg of NaBH$_3$CN in 15 ml of ethanol. Filter, then add 20 ml of water, 20 ml of ether, and stir for 1 hour with 15 ml of Dowex 50 (H+) ion exchange resin. Separate the water-resin layer, wash with ether, and charge to the top of a column containing 60 ml of Dowwex 50 (H+). Wash the column with water, then elute with 4% pyridine in water and methanol. Remove the solvent from the eluted product and purify the residue further by chromatography in methanol on LH-20 packing. Strip off the solvent from the appropriate fractions to obtain the desired product as a mixture of isomers. The pmr spectrum is in accord with the structure, and the mass spectrum of silylated material shows a molecular ion for the monosilylated product at m/e=711.

In the same manner, treatment of the substituted 3-aminoperhydrazepin-2-one described above with ethyl 4-(3-indolyl)-2-oxo-butyrate in the presence of NaBH$_3$CN affords 1-[(1-benzyloxycarbonyl-5-phthalimidyl)pentyl]-3-[(1-ethoxycarbonyl-3-(3-indolyl)propyl)amino]perhydroazepin-2-one.

EXAMPLE 17

1-[(1-Carboxy-5-phthalimidyl)pentyl]-3-[(1-carboxy-3-phenylpropyl)amino]perhydroazepin-2-one Hydrogenate a solution of 604 mg of the benzyl ester from Example 16 in 20 ml. of methanol for 20 hours over 0.15 g. of 10% Pd. on carbon. Filter and remove the solvent to obtain the desired diacid. The pmr is in accord with the structure and confirms the loss of the benzyl ester. The mass spectrum of silylated material shows molecular ions for the disilylated product at m/e=693 and for the trisilylated product at m/e=765.

Similarly, catalytic hydrogenation of 1-[(1-benzyloxycarbonyl-5-phthalimidyl)pentyl]-3-[(1-ethoxycarbonyl-3-(3-indolyl)propyl)amino]perhydroazepin-2-one, followed by the usual basic hydrolysis affords 1-[(1-carboxy-5-phthalimidyl)pentyl]-3-[(1-carboxy-3-(3-indolyl)propyl)amino]perhydroazepin-2-one.

EXAMPLE 18

1-[(1-Carboxy-5-amino)pentyl]-3-[(1-carboxy-3-phenylpropyl)amino]perhydroazepin-2-one Treat a solution of 489 mg. of the phthalimide of Example 17 in 10 ml. of methanol and 15 ml. of water with 260 mg of hydrazine hydrate under nitrogen at 70° for three hours. Cool, strip off the volatiles in vacuo, dissolve in 2 ml. of methanol, and filter off the phthalhydrazide. Chromatograph on LH-20 in methanol, and strip off the solvent from the appropriate fractions in vacuo to obtain the product.

The pmr spectrum is in accord with the structure and the mass spectrum of silylated material shows a peak at m/e=635 for the trisilylated product and at m/e=707 for the tetrasilylated product.

In a similar manner, treatment of 1-[(1-carboxy-5-phthalimidyl)pentyl]-3-[(1-carboxy-3-(3-indolyl)propyl)amino]perhydroazepin-2-one with hydrazine hydrate affords 1-[(1-carboxy-5-amino)pentyl]-3-[(1-carboxy-3-(3-indolyl)propyl)amino]perhydroazepin-2-one.

EXAMPLE 19

1-[(1-Benzyloxycarbonyl-5-phthalimidyl)pentyl]-3-(S)-(t-butoxycarbonylamino)perhydroazepin-3-one React 80.6 g. of 2-benzyloxycarbonyl-1,3-dithiane with 98.3 g. of N-4-bromobutyl-phthalimide in 130 ml. of DMF under nitrogen, by adding 15.2 g. of 50% sodium hydride emulsion (prewashed with petroleum ether) in 380 ml. of benzene over 65 minutes, keeping cold in an ice bath. Stir overnight at room temperature, add water and benzene, separate, wash with water and concentrate the organic layer to dryness in vacuo. Cleave the dithiane with N-bromosuccinimide in acetone followed by aqueous 5% sodium bicarbonate, concentrate, extract into 1:1 methylene chloride:hexane. Purify the ketoester by chromatography on silica in ethyl acetate:hexane 1:1.

Condense 5.0 g. of the keto-ester with 674 mg. of α-t-Boc-L-lysine in anhydrous ethanol in the presence of 5.4 g. of powdered 4A-molecular sieves under nitrogen, employing 600 mg. of sodium cyanoborohydride added over a 6-hour period by the method previously described. Purify the crude product by chromatography on LH-20 in methanol. Convert to the caprolactam by treatment with one equivalent of N-hydroxysuccinimide and a small excess of dicyclohexylcarbodiimide in methylene chloride at 0°; the reaction requires several days. Filter, concentrate to dryness, and purify the crude product by chromatography on silica gel with 7:3 hexane:ethyl acetate as eluant. The pmr of the product is consistent with its structure, and the mass spectrum has a molecular ion at m/e=577.

EXAMPLE 20

1-[1-Carboxy-2-(3-indolyl)ethyl]-3-(S)-[(1-carboxy-3-phenylpropyl)amino]perhydroazepin-2-one Methyl 3-[3-indolyl]-2-oxopropionate (1.09 g) and α-t-Boc-L-lysine (0.246) are dissolved in ethanol solvent containing powdered 4 Å molecular sieves (1.87 g). A solution of sodium cyanoborohydride (0.189 g) in ethanol is added at room temperature over six hours. When reaction is complete, the solvent is removed and the residue is partitioned between ether and water. The aqueous layer is isolated and pH adjusted to 3.6. The crude product is extracted into ethyl acetate and purified by LH-20 chromatography. Ring closure to 3-(S)-t-butoxycarbonylamino-1-[1-carbomethoxy-2-(3-indolyl)ethyl]perhydroazepin-2-one is carried out as described in Example 3. Saponificaton of the methyl ester and subsequent formic acid treatment to remove the t-butoxycarbonyl protecting group yields 3-(S)-amino-1-[1-carboxy-2-(3-indolyl)ethyl]perhydroazepin-2-one. 2-Oxo-4-phenylbutyric acid and this caprolactam are condensed in the presence of sodium cyanoborohydride to yield 1-[1-carboxy-2-(3-indolyl)ethyl]-3-(S)-[(1-carboxy-3-phenylpropyl)amino]perhydroazepin-2-one.

The silylated mass spectrum shows a parent ion at 693 m/e [3TMS+477 MWt], and loss of CH$_3$=678 m/e is observed.

EXAMPLE 21

1-[1-Carboxy-2-(4-hydroxyphenyl)ethyl]-3-(S)-[(1-carboxy-3-phenylpropyl)amino]perhydroazepin-2-one Methyl 3-(p-phydroxyphenyl)-2-oxopropionate and α-t-Boc-L-lysine are condensed in the presence of sodium cyanoborohydride as described in Example 19. Subsequent ring closure, saponification of methyl ester, and removal of the t-butoxycarbonyl group with formic acid gives 3-(S)-amino-1-[1-carboxy-2-(4-hydroxyphenyl)ethyl]perhydroazepin-2-one. The caprolactam and 2-oxo-4-phenylbutyric acid are condensed in the presence of sodium cyanoborohydride to yield 1-[1-carboxy-2-(4-hydroxyphenyl)ethyl]-3-(S)-[(1-carboxy-3-phenylpropyl)amino]perhydroazepin-2-one.

EXAMPLE 22

1-[1-Carboxy-2-phenylethyl]-3-(S)-[(1-carboxy-3-phenylpropyl)amino]perhydroazepin-2-one Methyl 2-oxo-3-phenylpropionate and α-t-Boc-L-lysine are condensed in the presence of sodium cyanoborohydride as described in Example 19. Subsequent ring closure to 3-(S)-t-butoxycarbonylamino-1-[1-carbomethoxy-2-phenylethyl]perhydroazepin-2-one is carried out as described in Example 3. Saponification of the methyl ester followed by removal of the t-butoxycarbonyl group affords 3-(S)-amino-1-[1-carboxy-2-phenylethyl]perhydroazepin-2-one. The caprolactam and 2-oxo-4-phenylbutyric acid are condensed in the presence of sodium cyanoborohydride to yield 1-[1-carboxy-2-phenylethyl]-3-(S)-[(1-carboxy-3-phenylpropyl)amino]perhydroazepin-2-one.

EXAMPLE 23

1-(1-Ethoxycarbonylethyl)-3-(S)-[(1-ethoxycarbonyl-3-phenylpropyl)amino]perhydroazepin-2-one A solution of 1-(1-carboxyethyl)-3-(S)-[(1-ethoxycarbonyl-3-phenylpropyl)amino]perhydroazepin-2-one (2.94 g.), a diastereoisomeric mixture prepared as in Example 13 from Isomer A of Example 12, with 40 ml. of ethanol was cooled to 0° and saturated with hydrogen chloride. After standing overnight at room temperature the solution was concentrated under vacuum. Dissolution in water, adjustment to pH 7, extraction with ether and concentration gave product as a colorless oil, weight 2.87 g. Tlc on silica gel indicated the presence of two diastereomers. If desired, the isomers may be separated by chromatography on silica gel and elution with hexane-ethyl acetate.

EXAMPLE 24

1-(1-Benzyloxycarbonylethyl)-3-(S)-[(1-ethoxycarbonyl-3-phenylpropyl)amino]perhydroazepin-2-one 3-(S)-t-Butoxycarbonylamino-1-(1-carboxyethyl)perhydroazepin-2-one (Isomer A), prepared in Example 12, is coverted to 1-(1-benzyloxycarbonylmethyl)-3-(S)-t-butoxycarbonylaminoperhydroazepin-2-one by the method of Wang, et al., *J. Org. Chem.*, 42, 1286 (1977), NMR: (CCl$_4$, TMS) δ1.3 (d, 3H); δ1.38 (S, 9H); δ1.7 (m, 6H); δ3.2 (broad, 2H); δ4.2 (m, 1H); 5.1 (q+s, 3H); δ5.8 (d, 1H); 7.2 (S, 5H).

$[\alpha]_D^{25} = -23.8$ (C=2.0, EtOH).

Removal of the t-butoxycarbonyl qroup in 4M HCl in ethyl acetate affords 3-(S)-amino-1-(1-benzyloxycarbonylethyl)perhydroazepin-2-one. NMR (D$_2$O, dioxane=3.67) δ1.2–2.1 (d+m, 9H); δ3.3 (broad, 2H); δ4.2 (m, 1H); δ4.6–5.0 (q+s, 3H); δ7.2 (s, 5H).
[α]$_D^{25}$ = −26.3 (C=2.2, EtOH).

A solution of 850 mg of this aminolactam, 2.14 g ethyl 2-oxo-4-phenylbutyrate and 267 mg sodium acetate is prepared in 8 ml ethanol. A solution of 490 mg sodium cyanoborohydride in 3 ml ethanol is added over 3.5 hr and stirring is continued overnight. The reaction is filtered and concentrated and the residue is partitioned between ethyl acetate and 5% sodium bicarbonate. The organic phase is washed with brine, dried and concentrated. The crude product is purified by chromatography over silica gel eluting with 3:2 hexane:ethylacetate affording the two diastereomers of 1-(1-benzyloxycarbonylethyl)-3-(S)-(1-ethoxycarbonyl-3-phenylpropyl-)aminoperhydroazepin-2-one. Isomer A (elutes first): [α]$_D^{25}$ = −26.6 (C=2.0, EtOH). NMR (CCl$_4$, TMS): δ1.0–2.0 (t+d+m, 14H) δ2.5–3.4 (m, 7H); δ4.1 (q, 2H); δ5.0–5.2 (s+m, 3H); δ7.1 (s, 5H); δ7.3 (s, 5H).

Isomer B (elutes second, major isomer): [α]$_D^{25}$ = −40.2 (C=2.0, EtOH).

NMR (CCl4, TMS): δ1.0–2.1 (t+d+m, 14H); δ2.1–3.0 (m, 4H); δ3.1–3.7 (m, 3H); δ1 (q, 2H); 5.0–5.2 (q+s, 3H); δ7.1 (s, 5H);.7.25 (s, 5H).

EXAMPLE 25

1-(1-Carboxyethyl)-3-[(3-phenyl-1-carboxamido-1-propyl) amino]perhydroazepin-2-one, ammonium salt A solution of 260 mg of 1-(1-carboxyethyl)-3-[(1-carbethoxy-3-phenyl-1-propyl)amino]perhydroazepin-2-one in 5 ml. of ethanol contained in a pressure vessel was cooled in an ice bath and saturated with ammonia gas at atmospheric pressure. The vessel was closed and kept at room temperature for 72 hours, at which time the reaction was complete as judged by thin layer chromatography. The solvent was removed by evaporation, and the product was lyophilized from water. Yield 200 mg.

Tlc: (silica plates, butanolacetic acidwaterethyl acetate 1:1:1:1) single spot, R$_f$=0.47.

EXAMPLE 26

1-(1-Carboxamidoethyl)-3-[(3-phenyl-1-carboxy-1-propyl) amino]perhydroazepin-2-one, ammonium salt This compound was made from the corresponding ethyl ester by a method similar to that described in the foregoing Example.

Tlc: (silica plates, butanol-acetic acid-water-ethyl acetate 1:1:1:1) single spot, R$_f$=0.60.

EXAMPLE 27

1-Carboxymethyl-3-[(1-carboxy-3-phenyl-1-propyl)amino]-7-methylperhydroazepin-2-one React 31.5 g. PCl$_5$ in 100 ml. benzene with 6.35 g. 2-methylcyclohexanone oxime following the procedure of Francis, *J. Am. Chem. Soc.*, 80, 6238 (1958) to obtain 3,3-dichloro-7-methylperhydroazepin-2-one. (m.p. 132.5°–134°).

Add a solution of 6.73 g. of this lactam in 35 ml. THF to a suspension of 0.86 g. NaH in 25ml. THF over 20 min. When hydrogen evolution ceases, add 8.70 g. t-butyl iodoacetate in 20 ml. THF over 30 min. When tlc indicates the reaction to be complete, add 50 ml. H$_2$O, separate the organic phase and wash with saturated (NH$_4$)$_2$SO$_4$ solution. Back wash the combined aqueous phases with ether, combine all organic phases and dry over Na$_2$SO$_4$. Filter and concentrate the filtrate in vacuo to obtain 1-t-butoxycarbonylmethyl-3,3-dichloro-7-methylperhydroazepin-2-one.

Nmr (CDCl$_3$, TMS): δ1.35 (d, 3H); δ1.45 (s, 9H); δ1.7–2.2 (m, 4H); δ2.6–2.9 (m, 2H); δ3.8–4.4 (m, 3H).

Hydrogenate a solution of 1.55 g. of this lactam in 10 ml. dioxane and 5 ml. H$_2$O containing 200 mg. MgO using 10% palladium on charcoal as catalyst. Filter the reaction, concentrate the filtrate in vacuo and partition the residue between H$_2$O and ether. Dry and concentrate the ether. Dry and concentrate the ether layer to obtain 1-t-butoxycarbonylmethyl-3-chloro-7-methylperhydroazepin-2-one as an oil.

Prepare an analytical sample by silica gel chromatography. Calc. (C$_{13}$H$_{22}$ClNO$_3$): C, 56.62; H, 8.04; N, 5.08. Found: C, 56.75; H, 8.18; N, 4.89.

Heat a solution of 7.0 g of this monochlorolactam and 3.10 g sodium azide in 70 ml DMF at 100° for 20 hr. Concentrate the reaction in vacuo and partition the residue between water and ether. Dry the ether layer and concentrate to the crude product. Chromatograph the crude product on silica gel using 7:3 hexane:ethyl acetate to obtain pure 3-azido-1-t-butoxycarbonylmethyl-7-methylperhydroazepin-2-one.

Ir: γ$_{N3}$, 2120 cm$^{-1}$; γ$_{CO}$, 1750 cm$^{-1}$, 1680 cm$^{-1}$.

Hydrogenate 5.1 g of this azide in 75 ml EtOH using 10% palladium on charcoal catalyst. Concentrate the filtered reaction mixture in vacuo to obtain the semicrystalline product as a mixture of diastereomers. Fractionally crystallize the crude product from ether-ethyl acetate to obtain the pure major diastereomer of 3-amino-1-t-butoxycarbonylmethyl-7-methylperhydroazepin-2-one. m.p. 117.5°–118°.

Obtain the minor diastereomer by chromatography of the residue from the mother liquors.

Hydrogenate a solution of 512 mg of the pure major diastereomer of 3-amino-1-t-butoxycarbonylmethyl-7-methylperhydroazepin-2-one, 618 mg ethyl 2-oxo-4-phenylbutyrate and 120 mg acetic acid in 20 ml ethanol using 10% palladium on charcoal as catalyst. Concentrate the filtered reaction mixture in vacuo and obtain the crude product. Purify the crude product by chromatography on silica gel using 1:1 ethyl acetate:hexane and isolate two diastereomeric racemates of 1-t-butoxycarbonylmethyl-3-[(1-ethoxycarbonyl-3-phenylpropyl)-amino]-7-methylperhydroazepin-2-one.

Racemate A (first to elute). Anal. Calc. (C$_{25}$H$_{38}$N$_2$O$_5$): C, 67.24; H, 8.58; N, 6.27. Found: C, 67.30 H, 8.71; N, 6.03. Mass spectrum: M+ =446; m/e: 389 (M+—C$_4$H$_9$); 373 (M+—C$_2$H$_5$CO$_2$); 317 (base, 373 —C$_4$H$_8$).

Racemate B (second to elute). Anal. Calc. (C$_{25}$H$_{38}$N$_2$O$_5$): C, 67.24; H, 8.58; N, 6.27. Found: C, 66.82; H, 8.55; N, 6.10. Mass spectrum: same as above.

Dissolve 380 mg. of racemate B in 2 ml. trifluoroacetic acid and store the solution for 2 hours at room temperature. Concentrate the reaction in vacuo, treat the residue with water and reconcentrate. Isolate 1-carboxymethyl-3-[(1-ethoxycarbonyl-3-phenylpropyl)amino]-7-methylperhydroazepin-2-one as the trifluoroacetate salt, m.p. 142°–145°.

Mass spectrum: M+ 390, m/e: 373 (M+—OH); 362 (M+—C$_2$H$_4$); 331 (M+—CH$_2$CO$_2$H); 317 (M+—CO$_2$C$_2$H$_5$).

Repeat the procedure on racemate A to obtain the isomeric monoester.

Dissolve 200 mg. of racemate B monoester trifluoroacetate in 2.5 ml. 1N NaOH and store the solution for 18 hr. at room temperature. Apply the reaction mixture to a column of Dowex 50 (H+), elute first with H₂O and then with 5% pyridine. Combine and concentrate the appropriate fractions and isolate 1-carboxymethyl-3-[(1-carboxy-3-phenylpropyl)amino]-7-methylperhydroazepin-2-one (racemate B), m.p. 215°–217° Dec.

Mass spectrum: M+ 362; m/e: 344 (M+—H₂O), 318 (M+—CO₂); 317 (M+—CO₂H).

Treat the monoester as described above and isoalte the diacid (racemate A).

Mass spectrum: M+ 362; m/e: 344 (M+—H₂O); 318 (M+—CO₂); 317 (M+—CO₂H).

Similarly, treat the minor diastereomer of 3-amino-1-t-butoxycarbonylmethyl-7-methylperhydroazepin-2-one as described above and isolate a second pair of diacids which are diastereomeric racemates.

The isomers of 1-carboxymethyl-3-[(1-ethoxycarbonyl-3-phenylpropyl)amino]-7-methyl perhydroazepin-2-one may each be converted to the corresponding diethyl esters by the method described in Example 22.

EXAMPLE 28

1-(1-Carboxyethyl)-3-(S)-[(1-carboxy-3-phenylpropyl)amino]perhydroazepin-2-one

The mixture of diastereomers of 1-(1-ethoxycarbonylethyl)-3-(S)-[(1-ethoxycarbonyl-3-phenylpropyl)amino]perhydroazepin-2-one (Example 23) is separated by chromatography on silica gel with hexane:ethyl acetate (7:3). Isolate two isomers of the diester. Isomer A (first to elute). NMR (CCl₄, TMS): 1.25 (m, 9H); δ1.4–2.2 (m, 8H); δ2.7 (m, 2H); δ3.2 (m, 4H); δ3.5 (s, 1H); δ4.2 (2xq, 4H); δ5.2 (q, 1H); δ7.2 (s, 5H). Isomer B. NMR (CCl₄, TMS): δ1.15 (t, 9H); δ1.4–2.2 (m, 8H); δ2.7 (m, 2H); δ3.1–3.7 (m, 4H); δ3.8 (s, 1H); δ4.1 (q, 4H); δ5.1 (q, 1H); δ7.2 (s, 5H).

Each of the isomeric esters is hydrolyzed in dilute sodium hydroxide. The hydrolysate is chromatographed over acidic ion exchange resin eluting with 5% pyridine in water. Concentration of the appropriate fractions affords the respective isomers of 1-(1-carboxyethyl)-3-(S)-[(1-carboxy-3-phenylpropyl)amino] perhydroazepin-2-one. Isomer A[α]$_{Na}^{25}$=37.0 (C=2.56, 0.1N NaOH) NMR (D₂O+NaOH, dioxane=δ3.8): δ1.33 (d, 3H, J=7 hz); δ1.4–2.3 (m, 8H); δ2.6–3.0(m, 2H); δ3.0–3.6(m, 4H); caδ4.8 (obscured by H₂O); δ7.4 (S, 5H) Isomer B: [α]$_{Na}^{25}$= −56.7° (C=2.82, 0.1N NaOH). NMR (D₂O+NaOD, dioxane=3.8), δ1.3 (d, 3H, J=7 hz); δ1.4–2.3 (m, 8H); 2.5–2.9 (m, 2H); δ3.1–3.8 (m, 4H); caδ0.48 (obscured by H₂O); δ7.3 (s, 5H).

EXAMPLE 29

1-(1-Carboxy-1-methylethyl)-3-(S)-[(1-carboxy-3-phenylpropyl)amino]perhydroazepin-2-one From 2-S-amino-6-hydroxyhexanoic acid [prepared according to Berlinguet and Gandry, *J. Biol. Chem.*, 198, 765 (1952)] prepare the N-t-butoxycarbonyl derivative using the procedure of Otuska et al., *Bull. Chem. Soc. Japan*, 39, 1171 (1966)]. Convert this protected derivative to the O-p-toluenesulfonate benzyl ester [D. Theodoropoulos et al., *Biochemistry* 6, 3927 (1967)]. Heat this diester with excess ethyl 2-aminoisobutyrate in toluene. Purify the crude reaction product chromatographically on silica gel and isolate Nα-t-butoxycarbonyl-Nε-(2-ethoxycarbonyl-2-propyl)-lysine benzyl ester. Remove the benzyl ester using standard hydrogenolysis conditions and cyclize the resulting acid using dicylohexylcarbodiimide and N-hydroxysuccinimide as described in Example 3. After purification of the lactam, react it with ethyl 2-oxo-4-phenylbutyrate and hydrogen as described in Example 1. Purify the resulting diester by chromatography and isolate the diastereomers. Hydrolyze each of the diastereomeric diesters with 1M NaOH and purify the diacids by ion exchange chromatography.

EXAMPLE 30

1-(1-Carboxyethyl)-3-(S)-(1-ethoxycarbonyl-3-phenylpropyl)aminoperhydroazepin-2-one The diastereomers described in Example 24 are catalytically dibenzylated over palladium on carbon in aqueous dioxane to afford the respective diastereomers of 1-(1-carboxyethyl)-3-(S)-(1-ethoxycarbonyl-3-phenylpropyl)aminoperhydroazepin-2-one.

Isomer A: [α]$_D^{25}$= −22.3° (C=2.2, EtOH); m.p. 132–134. NMR (CDCl₃, TMS): δ1.1–1.5 (d=t, 6H); 1.5–2.3 (m, 8H); 2.5–3.0 (m, 2H); 3.35 (m, 4H); 4.2 (q, 2H); 5.1 (q, 1H); 6.65 (s, 2H); 7.2 (s, 5H).

Anal. (C₂₁H₃₀N₂O₅): Calc.: C, 64.59; H, 7.74; N, 7.18. Found: C, 64.20; H, 7.74; N, 6.70.

Isomer B: [α]$_D^{25}$= −39.9 (C=3.1, EtOH): m.p. 110–113 (EtOAc). NMR (CDCl₃, TMS): δ1.2–1.5 (d=t, 6H); 1.5–2.3 (m, 8H); 2.6–2.9 (m, 2H); 3.2–3.7 (m, 4H); 4.2 (q, 2H); 5.1 (q, 1H); 7.2 (s, 7H).

Anal. (C₂₁H₃₀N₂O₅): Calc.: C, 64.59; H, 7.74; N, 7.18. Found: C, 64.18; H, 7.74; N, 6.93.

EXAMPLE 31

Diesters of Formula I derived from 3-(S)-amino-1-(1-ethoxycarbonylethyl)perhydroazepin-2-one 3-(S)-Amino-1-(1-ethoxycarbonylethyl)perhydroazepin-2-one (prepared as described in Examples 12 and 13 from Isomer A) is reductively condensed with the following α-ketoesters (Table I) in place of ethyl 2-oxo-4-phenylbutyrate using the palladium on charcoal method as described in Example 27. Work up and purification as described in this example affords the corresponding diesters listed in Table II.

Alternatively, sodium cyanoborohydride may be used in the reductive condensation as described in Example 24.

EXAMPLE 32

Diacids of Formula I derived from 3-(S)-amino-1-(1-carboxyethyl)perhydroazepin-2-one Saponification of the diesters listed in Table II using the procedure described in Example 3 including purification gives the products of Formula I described in Table II wherein R, R², R⁵, R⁶=H, R³=CH₃, R⁴=OH.

Alternatively, reductive condensation of 3-(S)-amino-1-(1-carboxyethyl)perhydroazepin-2-one (Example 12) with the α-ketoacids listed in Table III following the procedure described in Example I affords the products of Formula I described above.

EXAMPLE 33

Monoesters of Formula I derived from 3-(S)-amino-1-(1-carboxyethyl)perhydroazepin-2-one Reductive condensation of the α-ketoesters listed in Table I with 3-(S)-amino-1-(1-carboxyethyl)perhydroazepin-2-one (Isomer A) as described in Example 3 affords the products of Formula I listed in Table II wherein $R^2$, $R^5$, $R^6$=H and $R^3$=CH$_3$, $R^4$=OH.

EXAMPLE 34

Monoesters of Formula I derived from 3-amino-1-carboxymethyl-7-methylperhydroazepin-2-one The major diastereomer of 3-amino-1-t-butoxycarbonylmethyl-7-methylperhydroazepn-2-one (Example 27) is reductively condensed with the α-ketoesters listed in Table I using either the palladium catalyzed reduction method (Example 27) or the sodium cyanoborohydride procedure (Example 24). Chromatographic purification of the products followed by removal of the t-butyl ester (Example 27) affords the compounds of Formula I listed in Table II wherein $R^2$=CH$_3$; $R^3$, $R^5$, $R^6$=H and $R^4$=OH.

EXAMPLE 35

Diacids of Formula I derived from 3-amino-1-carboxymethyl-7-methylperhydroazepin-2-one Saponification of the monoesters prepared in Example 34 using the procedure described in Example 3, including purification, gives the products of Formula I described in Table II wherein $R^3$, $R^5$, $R^6$=H; $R^2$=CH$_3$; R, $R^4$=OH.

Alternatively, the t-butyl ester of the major diastereomer of 3-amino-1-t-butoxycarbonylmethyl-7-methylperhydroazepin2-one may be cleaved with trifluoroacetic acid to afford 3-amino-1-carboxymethyl-7-methylperhydroazepin-2-one. Reductive condensation of this compound with the α-ketoacids listed in Table III following the procedure described in Example I affords the products of Formula I described above.

EXAMPLE 36

Monoesters of Formula I derived from 3-amino-1-carboxymethyl-7-methylperhydroazepin-2-one Reductive condensation of the α-ketoesters listed in Table I with 3-amino-1-carboxymethyl-7-methylperhydroazepin-2-one (Example 35) using the conditions described in Examples 24 or 27 affords the products of Formula I listed in Table II wherein $R^3$, $R^5$=H, $R^2$=CH$_3$, $R^4$=OH.

TABLE I

| | | α-Ketoesters |
|---|---|---|
| a. | Benzyl | 2-oxo-4-phenylbutyrate |
| b. | Ethyl | 4-p-chlorophenyl-2-oxobutyrate |
| c. | Ethyl | 4-(3-indolyl)-2-oxobutyrate |
| d. | Ethyl | 2-oxo-4-(2-thienyl)butyrate |
| e. | Ethyl | 2-oxo-4-(2-naphthyl)butyrate |
| f. | Ethyl | 4-p-hydroxyphenyl-2-oxobutyrate |
| g. | Ethyl | phenoxypyruvate |
| h. | Ethyl | 2-oxo-5-phenylpentanoate |
| i. | Ethyl | 4-p-methoxyphenyl-2-oxobutyrate |
| j. | Ethyl | 5-methyl-2-oxohexanoate |
| k. | Benzyl | 2-oxo-6-phthalimidohexanoate |

TABLE II

Products of Formula I
($R_2$, $R_5$ = H; $R_3$ = CH$_3$)

| | R | $R_1$ | $R_4$ |
|---|---|---|---|
| l. | benzyloxy | phenylethyl | ethoxy |
| m. | ethoxy | p-chlorophenethyl | ethoxy |
| n. | ethoxy | 3-indolylethyl | ethoxy |
| o. | ethoxy | 2-thienylethyl | ethoxy |
| p. | ethoxy | 2-naphthylethyl | ethoxy |
| q. | ethoxy | p-hydroxyphenethyl | ethoxy |
| r. | ethoxy | phenoxymethyl | ethoxy |
| s. | ethoxy | 3-phenylpropyl | ethoxy |
| t. | ethoxy | p-methoxyphenethyl | ethoxy |
| u. | ethoxy | 3-methylbutyl | ethoxy |
| v. | benzyloxy | 4-phthalimidobutyl | ethoxy |
| w. | benzyloxy* | 4-aminobutyl | ethoxy |

*after hydrazinolysis

TABLE III

| | α-Ketoacids |
|---|---|
| x. | 2-oxo-4-phenylbutyric acid |
| y. | 4p-chlorophenyl-2-oxobutyric acid |
| z. | 4-(3-indolyl)-2-oxobutyric acid |
| aa. | 2-oxo-4-(2-thienyl)butyric acid |
| bb. | 2-oxo-4-(2-naphthyl)butyric acid |
| cc. | 4-p-hydroxyphenyl-2-oxobutyric acid |
| dd. | phenoxypyruvic acid |
| ee. | 2-oxo-5-phenylpentanoic acid |
| ff. | 4-p-methoxyphenyl-2-oxobutyric acid |
| gg. | 5-methyl-2-oxohexanoic acid |
| hh. | 2-oxo-6-phthalimidohexanoic acid |

EXAMPLE 37

Monoesters of Formula I derived from 3-(S)-amino-1-(1-carboxyethyl)perhydroazepin-2-one Reaction of 3-(S)-amino-(1-1-benzyloxycarbonylethyl)perhydroazepin-2-one (Example 24) or 3-(S)-amino-1-(1-ethoxycarbonylethyl)perhydroazepin-2-one (Example 13) with some of the ketoacids from Table III using the procedure of Example 2 affords the products of Formula I($R^2$, $R^5$=H; $R^3$=CH$_3$, R=OH) listed in Table IV.

TABLE IV

Monoesters of Formula I

| | $R^1$ | $R^4$ |
|---|---|---|
| ii. | p-chlorophenethyl | benzyloxy |
| jj. | 2-naphthylethyl | benzyloxy |
| kk. | 3-methylbutyl | benzyloxy |
| ll. | 4-aminobutyl* | benzyloxy |
| mm. | phenethyl | ethoxy |
| nn. | phenethyl | benzyloxy |

*after hydrazinolysis

EXAMPLE 38

Monoesters of Formula I derived from 3-amino-1-carboxymethyl-7-methylperhydroazepin-2-one Reaction of the major isomer of 3-amino-1-t-butoxymethyl-7-methylperhydroazepin-2-one with benzyl alcohol and thionyl chloride yields 3-amino-1-benzyloxymethyl-7-methylperhydroazepin-2-one hydrochloride, which after treatment with base, yields the free amino ester. Reaction of this amino ester as described in Example 37 affords the products of Formula I ($R^3$, $R^5$, $R^6$=H; $R^2$=CH$_3$; R=OH) listed in Table IV.

Alternatively, use of ethanol in place of benzyl alcohol affords the corresponding ethyl esters listed in Table IV and described above.

EXAMPLE 39

1-(1-Benzyloxycarbonylethyl)-3-(S)-(1-carboxy-3-phenylpropyl)aminoperhydroazepin-2-one A solution of 490 mg sodium cyanoborohydride in 3 ml ethanol is added over 2.5 hrs to a solution of 2.43 g t-butyl 2-oxo-4-phenylbutyrate, 850 mg 1-(1-benzyloxycarbonylethyl)-3-(S)-aminoperhydroazepin-2-one hydrochloride (from Isomer A, Example 24) and 267 mg sodium acetate in 10 ml ethanol. The reaction is stirred at room temperature overnight, filtered and concentrated. The residue is partitioned between ethyl acetate and 5% sodium bicarbonate. After drying, concentration of the organic phase affords a residue which is chromatographed over silica gel with hexane-ethyl acetate (7:3) giving the pure diastereomers of 1-(1-benzyloxycarbonylethyl)-3-(S)-(1-t-butoxycarbonyl-3-phenylpropyl)aminoperhydroazepin-2-one.

Isomer A (elutes first): $[\alpha]_{Na}^{25} = -24.6°$ (C=2, EtOH)

Isomer B (elutes second): $[\alpha]_{Na}^{25} = -31.1°$ (C=2, EtOH).

Treatment of each of these isomers with HCl-EtOAc affords 1-(1-benzyloxycarbonylethyl)-3-(S)-(1-carboxy-3-phenylpropyl)aminoperhydroazepin-2-one hydrochloride.

Isomer A: $[\alpha]_{Na}^{25} = -51.4°$ (c=2, EtOH).
Isomer B: $[\alpha]_{Na}^{25} = -15.7°$ (c=2, EtOH).

NMR (DMSO-d$_6$): $\delta$1.2–2.1 (m+d, J=7 hz); $\delta$2.4–2.9 (m, partially obscured by DMSO); $\delta$3.0–4.0 (m); $\delta$4.9 (q, J=7 hz); $\delta$5.1 (s); $\delta$7.0 (broad), $\delta$7.2 (s); $\delta$7.35 (s).

EXAMPLE 40

1-Carboxymethyl-3-(1-carboxy-3-phenylpropyl)amino-7-phenylperhydroazepin-2-one

To a solution of 25 g phosphorus pentachloride in 220 ml CH$_2$Cl$_2$ kept at 0° is added a solution of 22 g 7-phenylcaprolactam and 18.9 g pyridine in 220 ml CH$_2$Cl$_2$. Portionwise addition of 45.1 g phenyltrimethylammonium tribromide is followed by allowing the reaction mixture to reach room temperature. After 3 hours, the reacton mixture is poured into ice water and extracted with CH$_2$Cl$_2$. The organic phase is washed with 5% aqueous sodium bisulfite. After drying and concentration, the crude residue is purified by chromatography over silica gel eluting with ethyl acetate:hexane (2:3). Concentration of the appropriate fractions affords 16.3 g. 3-bromo-7-phenylperhydroazepin-2-one as a mixture of diastereomers.

A solution of 15.5 g of this lactam and 14.7 t-butyl iodoacetate in 150 ml tetrahydrofuran is added dropwise to a slurry of 1.45 g sodium hydride in 20 ml tetrahydrofuran. After 3 hr at room temperature the reaction is quenched by the addition of 15 ml sat. NH$_4$Cl solution. The mixture is filtered and concentrated and the residue is partitioned between CHCl$_3$ and H$_2$O. The crude product is obtained after drying and concentrating the CHCl$_3$ solution. Chromatography over silica gel with hexane: ethyl acetate (4:1) affords two isomers of 3-bromo-1-t-butoxycarbonylmethyl-7-phenylperhydroazepin-2-one: isomer A (minor, elutes first), and isomer B (major, elutes second).

A solution of 20 g of isomer B and 7.69 g lithium azide in 100 ml dimethylformamdie is heated at 80° overnight. After concentration, the residue is partitioned between water and ethyl acetate. The organic phase is dried and concentrated to afford 3-azido-1-t-butoxycarbonylmethyl-7-phenylperhydroazepin-2-one which may be recrystallized from ethyl acetate-hexane.

NMR (CDCl$_3$, TMS): $\delta$1.45 (s, 9H); $\delta$1.6–2.7 (m, 6H); $\delta$3.3 (d, 1H, J=17 hz); $\delta$4.0 (d, 1H, J=17 hz); $\delta$4.4 (broad m, 1H); $\delta$4.8 (broad d, 1H); $\delta$7.25 (s, 5H).

A solution of 8.95 g of this azide in 75 ml ethanol is hydrogenated over 2 g 10% Pd-C at 45° C. for 5 hr. The soluion is then filtered and concentrated to afford 8.3 g 3-amino-1-t-butoxycarbonylmethyl-7-phenylperhydroazepin-2-one. NMR (CDCl$_3$, TMS): $\delta$1.4 (s, 9H); $\delta$1.7–2.5 (m+s, 8H); $\delta$3.4 (d, 1H, J=17 hz); $\delta$3.95 (d, 1H, J=17 hz); $\delta$4.0 (broad m, 1H); $\delta$4.95 (broad d, 1H); $\delta$7.3 (s, 5H).

A solution of 3.8 g of this amine, 3.7 g ethyl 2-oxo-4-phenylbutyrate and 0.68 ml acetic acid in 50 ml ethanol is hydrogenated and the isomers separated as described in Example 27 to afford 1-t-butoxycarbonylmethyl-3-(1-ethoxycarbonyl-3-phenylpropyl)amino-7-phenylperhydroazepin-2-one:

Isomer A (elutes first) and isomer B (elutes second).

Each of the above isomers is treated with trifluoroacetic acid to afford the respective isomers of 1-carboxymethyl-3-(1-ethoxycarbonyl-3-phenylpropyl) amino-7-phenyperhydroazepin-2-one as the trifluoroacetate salt.

Isomer A: NMR (CDCl$_3$, TMS): $\delta$1.3 (t); $\delta$1.5–2.6 (m); $\delta$2.6–3.1 (m); $\delta$3.6–3.9 (m); $\delta$4.2 (q); $\delta$4.0–4.8 (m); $\delta$7.2 (s); $\delta$8.9 (broad s).

Isomer B: NMR (DMSO-d$_6$, TMS): $\delta$1.27 (t); $\delta$1.6–3.1 (m); $\delta$3.7–4.5 (m+q); $\delta$4.7 (broad); $\delta$5.1 (broad); $\delta$7.2 (s); $\delta$7.3 (s).

Each of the above isomers is treated with dilute sodium hyroxide, then purified by chromatography over acid ion exchange resin to afford the corresponding isomers of 1-carboxymethyl-3-(1-carboxy-3-phenylpropyl)amino-7-phenylperhydroazepin-2-one.

Isomer A: NMR (D$_2$O+NaOD, dioxane=$\delta$3.80): $\delta$1.6–2.3 (broad m); $\delta$2.55–2.9 (m); $\delta$3.25 (t); $\delta$3.5–3.8 (m); $\delta$4.6–5.1 (broad, obscured by H$_2$O); $\delta$7.3 (s); $\delta$7 35 (s).

Isomer B: NMR (D$_2$O+NaOD, dioxane=$\delta$3.80): 1.5–2.3 (broad m); $\delta$2.5–2.9 (m); $\delta$3 25 (t); $\delta$3.6 (broad s); $\delta$3.7–4.2 (m); $\delta$4.5–5.2 (m, obscured by H$_2$O); $\delta$7.25 (s); $\delta$7.35 (s).

Similarly, treat the minor diastereomer of 3-bromo-1-t-butoxycarbonylmethyl-7-phenylperhydroazepin-2-one as described above and isolate a second pair of diacids which are diastereomeric racemates.

EXAMPLE 41

R$^2$-Substituted Products of Formula I

By treatment with PCl$_5$ or PBr$_5$ in benzene or by following the procedure decribed at the beginning of Example 40 but replacing the 7-phenylperhydroazepin-2-one employed therein by perhydroazepin-2-ones substituted in the 7 position by the groups listed in Table V, the corresponding 7-substituted 3-bromo-perhydroazepin-2-ones could be obtained. By further treatment as described in Example 40 esters could be obtained of Formula I where R=OC$_2$H$_5$, R$_1$=CH$_2$CH$_2\phi$, R$_3$=R$_5$=H, R$_4$=OH, and R$_2$=the groups listed in Table V.

By additional treatment as described in Example 40, the corresponding diacids could be obtained, where R=OH, R$_1$=CH$_2$CH$_2\phi$, R$_3$=R$_5$=H, R$_4$=OH, and R$_2$=the groups listed in Table V. The stereochemical consequences in these cases parallel those described in the examples quoted.

TABLE V

| 7-Substituted Perhydroazepin-2-ones |
|---|
| $R_2 =$ —$C_2H_5$ |
| -n-$C_4H_9$ |
| -cyclohexyl |
| -benzyl |
| -(1-piperidino)methyl |
| -p-tolyl |
| -p-anisyl |
| -p-chlorophenyl |
| -(2-pyridyl) |

[All these compounds are described in the chemical literature]

EXAMPLE 42

$R^2$-Aminoalkyl Substituted Products of Formula I

Perhydroazepin-2-ones substituted in the 7-position by 2-aminoethyl or 4-aminobutyl groups, both of which are described in the chemical literature, could be converted to the corresponding phthalimido derivative at their primary amine functionality by well-known methods, and the resulting compounds treated a described in Example 40 to afford diesters of Formula I where $R=OC_2H_5$, $R_1=CH_2CH_2\phi$, $R_3=R_5=H$, $R_4=O$-t-butyl, and $R_2$ represents

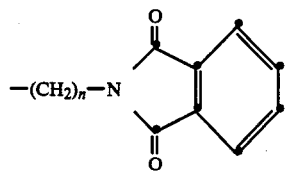

where n=2 or 4, respectively. Careful hydrazinolysis would remove the phthalimide protecting group, affording the corresponding diesters, which could be treated with trifluoracetic acid as described in Example 40 to afford the monoesters of Formula I where $R=OC_2H_5$, $R_1=CH_2CH_2\phi$, $R_3=R_5=H$, $R_4=OH$ and $R_2=(CH_2)_uNH_2$ where u=2 or 4. Basic hydrolysis as described in the example quoted would afford the corresponding diacids of Formula I where $R=R_4=OH$, $R_1=CH_2CH_2\phi$, $R_3=R_5=H$ and $R_2=(CH_2)_n-NH_2$ where n=2 or 4.

The stereochemical consequences in these cases parallel those described in the example quoted.

EXAMPLE 43

A typical tablet contains 1-(1(S)-carboxyethyl)-3-(S)-[(1(S)-ethoxycarbonyl-3-phenylpropyl)amino]perhydroazepin-2-one (25 mg.), pregelatinized starch USP (82 mg.), microcrystalline cellulose (82 mg.) and magnesium stearate (1 mg.). In like manner, for example, 1-(1(S)-carboxyethyl)-3-(S)-[(1(S)-carboxy-5-amino-1-pentyl)amino]perhydroazepin-2-one (20 mg.) may be formulated in place of 1-(1(S)-carboxyethyl)-3-(S)-[(1(S)-ethoxycarbonyl-3-phenylpropyl)amino] perhydroazepin-2-one with the composition of pregelatinized starch, microcrystalline cellulose and magnesium stearate described above.

EXAMPLE 44

Compressed Tablet containing 5 mg. of active ingredient

|  | Per tablet, Mg. |
|---|---|
| 1(S)—Carboxyethyl-3-(S)—[(1(S)—ethoxycarbonyl-3-phenylpropyl)-amino]-perhydroazepin-2-one | 5 |
| Calcium phosphate dibasic | 245 |
| Ethyl cellulose (as 5% solution in ethanol) | 5 |
| Unmixed granulation | 255 |
| Add: | |
| Starch, corn | 14 |
| Magnesium stearate | 1 |
|  | 270 |

Directions: Mix the active ingredient above and calcium phosphate and reduce to a No. 60 mesh powder. Granulate with Ethocel in alcohol and pass the wet granulation through a No. 10 screen. Dry the granulation at 110° F. for 12–18 hours. Dry grind to a No. 20 mesh. Incorporate the "adds" and compress into tablets each weighing 270 mg.

EXAMPLE 45

Dry filled capsule containing 5 mg. of active ingredient.

|  | Per capsule, mg. |
|---|---|
| 1-Carboxymethyl-3-(S)—[1(S)—ethoxy-carbonyl-3-phenyl-propyl]amino-7(S)—phenyl-perhydroazepin-2-one | 5 |
| Lactose | 273 |
| Magnesium stearate | 2 |
| Mixed powders | 280 |

Mix the active ingredient above, lactose, and magnesium stearate and reduce to a No. 60 mesh powder. Encapsulate, filling 280 mg. in each No. 2 capsule.

The above formulations can be employed to prepare compressed tablets or capsules of other novel compounds of this invention hereinbefore described.

While the above examples describe the preparation of certain compounds which are illustrative of the novel compounds of this invention and certain specific dosage forms suitable for administering the novel compounds, it is to be understood that the invention is not to be limited to the specific compounds described in the examples or by the specific reaction conditions described for the preparation of these compounds or by the specific ingredients included in the pharmaceutical preparations, but is to be understood to embrace variations and modifications thereof.

What is claimed is:

1. The compound:

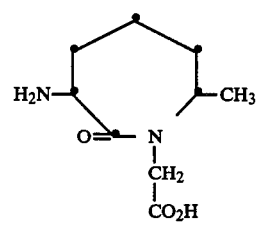

and the lower alkyl and benzyl esters thereof.
2. The compound:
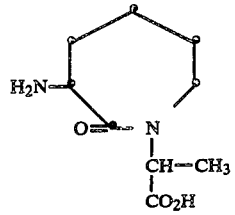
and the lower alkyl and benzyl esters thereof.
3. The compound:
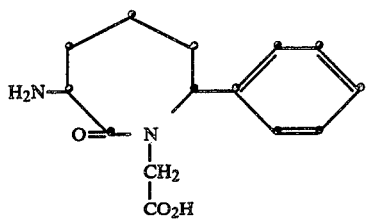
and the lower alkyl and benzyl esters thereof.
* * * * *